US006008425A

United States Patent [19]
Mohr et al.

[11] Patent Number: 6,008,425
[45] Date of Patent: Dec. 28, 1999

[54] PROCESS FOR ISOMERIZATION OF ALKYLAROMATIC HYDROCARBONS

[75] Inventors: Gary D. Mohr, League City, Tex.; Johannes Petrus Verduijn, Bertem, Belgium

[73] Assignee: Exxon Chemical Patents Inc., Houston, Tex.

[21] Appl. No.: 08/865,632

[22] Filed: May 29, 1997

Related U.S. Application Data

[60] Provisional application No. 60/018,550, May 29, 1996.

[51] Int. Cl.$^6$ .................... C07C 5/22; B01J 29/06
[52] U.S. Cl. .................. 585/481; 585/480; 502/67
[58] Field of Search .................. 585/481, 480; 502/67

[56] References Cited

U.S. PATENT DOCUMENTS

| | | | |
|---|---|---|---|
| 3,997,618 | 12/1976 | Cornely et al. | 260/668 A |
| 4,229,424 | 10/1980 | Kokotailo | 423/328 |
| 4,381,256 | 4/1983 | Hildebrandt | 502/68 |
| 4,582,815 | 4/1986 | Bowes | 502/64 |
| 4,740,650 | 4/1988 | Pellet et al. | 585/480 |
| 4,847,224 | 7/1989 | Fajula et al. | 502/67 |
| 5,145,659 | 9/1992 | McWilliams | 423/713 |
| 5,516,956 | 5/1996 | Abichandani et al. | 585/481 |

FOREIGN PATENT DOCUMENTS

| | | | |
|---|---|---|---|
| 11059/35A | 8/1995 | China | B01J 20/18 |
| 0109962 | 6/1984 | European Pat. Off. . | |
| 0110650 | 6/1984 | European Pat. Off. | C01B 33/28 |
| 0284206 | 9/1988 | European Pat. Off. | C01B 33/28 |
| 0323892 | 12/1989 | European Pat. Off. | C01B 33/28 |
| 92/12928 | 6/1992 | WIPO | C01B 33/34 |
| WO 96/16004 | 5/1996 | WIPO . | |

OTHER PUBLICATIONS

"Tructure Type Index"; internet search document; pp. 1–10, Apr. 1998.
"MFI"; internet document; pp. 1–3, Apr. 1998.
"MEL"; internet search document; pp. 1–3, Apr. 1998.
U.S. application No. 08/561,674, filed Nov. 22, 1995.
U.S. application No. 08/865,343, filed May 29, 1997.
Chemical Abstracts, vol. 101, No. 9, Aug. 27, 1984 Columbus, Ohio, US; Abstract No. 72405n, p. 614.
Chemical Abstracts, vol. 85, No. 13, Sep. 27, 1976 Columbus, Ohio, US; Abstract No. 94018s, p. 604.
U.S. application No. 08/865,633, Dan E. Hendriksen et al., filed May 29, 1997.

*Primary Examiner*—Walter D. Griffin
*Assistant Examiner*—Thuan D. Dang
*Attorney, Agent, or Firm*—Edward F. Sherer

[57] ABSTRACT

A process for isomerizating a feed containing alkylaromatic hydrocarbons, e.g., monocyclic alkylaromatic hydrocarbons and/or bicyclic alkylaromatic hydrocarbons. The process is carried out by contacting the feed under conversion conditions with a zeolite bound zeolite catalyst which comprises first crystals of an intermediate pore size first zeolite and a binder which comprises second crystals of a second zeolite. The process finds particular applications in isomerizing a feed containing ethylbenzene and less than equilibrium amounts of xylenes with ethylbenzene and can produce a product containing above equilibrium quantities of para-xylene and low aromatics ring loss and xylene loss.

52 Claims, No Drawings

PROCESS FOR ISOMERIZATION OF ALKYLAROMATIC HYDROCARBONS

This applications claims the benefit of U.S. provisional application No. 60/018,550, filed on May 29, 1996.

FIELD OF THE INVENTION

This invention relates to a process for the isomerization of alkylaromatic hydrocarbons using a zeolite bound zeolite catalyst. More particularly, but not by way of limitation, this invention relates a process for the isomerization of ortho- and meta-xylenes to para-xylene, as well as the removal of ethylbenzene from a $C_8$ aromatics stream using a zeolite bound zeolite catalyst.

BACKGROUND OF THE INVENTION

Xylenes are valuable industrial chemicals. Sources of xylenes include catalytic reformate, pyrolysis gasoline, toluene disproportionation; $C_7$–$C_9$ aromatic transalkylation, and the like. For example, catalytic reforming hydrocarbon feeds such as naphtha using conventional aromatization catalysts produces a reformate which is richer in the content of $C_6$–$C_{10}$ aromatics than the feeds. Of these aromatics, significant quantities of $C_8$ aromatics are produced which comprise a mixture of ethyl benzene, and mixed ortho-, meta- and para-xylene isomers. Typically, the product from the catalytic reformer (reformate) is fed to an aromatic extraction plant where the aromatics, e.g., $C_6$, $C_7$ and $C_8$ aromatics, are separated from the paraffins and other non-aromatic products present in the reformate. The $C_8$ aromatic fraction may then be separated from the lower boiling $C_6$ and $C_7$ aromatics by distillation.

The $C_8$ aromatic fraction normally contains a mixture of ethyl benzene and the ortho-, para-, and meta-xylene isomers. The three xylene isomers are usually present in near thermodynamic equilibrium amounts, e.g., generally 52–53 wt. % meta-xylene, 23–24 wt. % para-xylene and 23.5 to 24.5 wt. % ortho-xylene. Of the xylene isomers, meta-xylene is typically the least desired product. Because para-xylene is of particular value as a chemical intermediate in a number of applications, it may be desirable to separate the para-xylene from the other isomers using conventional techniques such as crystallization, or by adsorption/desorption on zeolites. After such separation, the residual $C_8$ aromatic fraction contains non-equilibrium quantities of ethylbenzene and the mixed ortho- and meta-xylene isomers and is lean with respect to para-xylene content.

The para-xylene lean residual product may be further upgraded by subjecting it to isomerization conditions wherein at least a portion of the ethylbenzene is converted to other products such as diethylbenzene or benzene and ethane and a portion of the ortho- and meta-xylenes are isomerized to produce a mixture which once again approximates the equilibrium concentration of the ortho-, meta-, and para-xylene isomers. Typically such isomerization conditions comprise contacting the non-equilibrium $C_8$ aromatic feed with a suitable isomerization catalyst in a suitable reactor at temperatures above about 600° F. and preferably at pressures sufficient to maintain the reaction in the vapor phase.

A commercially viable xylene isomerization process must exhibit high xylene isomerization activity and, also, must produce the desired product without a significant loss of xylenes. The loss of xylene is a result of undesired side-reactions, involving hydrogenation of the aromatic ring, hydrogenolysis, demethylation, and particularly disproportionation and transalkylation.

Another factor of importance in a xylene isomerization process is the effect that ethylbenzene has on the entire isomerization and xylene recovery loop. When ethylbenzene is present in appreciable quantities in the feed to the isomerization process, it will accumulate in the loop unless it is excluded from the feed or converted by some reaction in the loop to products which are separable from xylenes. Ethylbenzene can be separated from the xylenes by "superfractionation", but this procedure is very expensive. A more desirable method of eliminating the ethylbenzene is through a conversion reaction taking place simultaneously with the isomerization reaction of the xylenes. One method of converting ethylbenzene is to isomerize the ethylbenzene to xylenes. It is often desirable that the ethylbenzene conversion reaction be a deethylation reaction producing benzene and ethane rather than a disproportionation reaction to benzene and diethylbenzene. The deethylation reaction preserves more xylenes and produces a high quality reaction product.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Numerous processes have been proposed for the isomerization of xylene feeds using zeolite catalysts. For instance, U.S. Pat. No. 4,312,790 involves a xylene isomerization process using an alumina bound zeolite catalyst. U.S. Pat. No. 4,939,110 involves a xylene isomerization process using a zeolite catalyst such as a ZSM-5 which is bound by a binder material such as alumina, silica, or clay.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using the powder in commercial processes, the zeolite crystals are usually bound.

The zeolite powder is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the zeolite be resistant to mechanical attrition, that is, the formation of fines which are small particles, e.g., particles having a size of less than 20 microns.

Although such bound zeolite aggregates have much better mechanical strength than the zeolite powder, when such a bound zeolite is used for xylene isomerization, the performance of the zeolite catalyst, e.g., activity, selectivity, activity maintenance, or combinations thereof, can be reduced because of the binder. For instance, since the binder is typically present in an amount of up to about 50 wt. % of zeolite, the binder dilutes the adsorption properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in xylene isomerization. Furthermore, when the bound zeolite is used in xylene isomerization, the binder may affect the chemical reactions that are taking place within the zeolite and also may itself catalyze undesirable reactions which can result in the formation of undesirable products.

SUMMARY OF THE INVENTION

The present is directed to a process for the isomerization of isomerizable alkylaromatic hydrocarbons utilizing a zeolite bound zeolite catalyst which comprises first crystals of a first intermediate pore size zeolite, and a binder comprising second crystals of a second zeolite.

In another embodiment, the present invention provides a process for isomerizing a non-equilibrium feed mixture containing ethylbenzene and xylene isomers comprising contacting said feed mixture under xylene isomerization conditions with the zeolite bound zeolite catalyst.

In a further embodiment of the invention, the present invention provides a process for isomerizating a non-equilibrium feed mixture containing ethylbenzene and xylene isomers comprising contacting said feed steam with the zeolite bound zeolite catalyst to partially convert the ethylbenzene and then contacting the resulting feed with a second catalyst to isomerize the xylene isomers.

The isomerization of xylene streams in accordance with the process of the invention gives rise to an isomerization product which contains about equilibrium quantities or above of para-xylene with a very low percent of xylene loss. In addition, ethylbenzene present in the xylene streams is substantially converted, i.e., at least 30%, preferably greater than 50%, of the ethylbenzene is converted.

DETAILED DESCRIPTION OF THE INVENTION

The zeolite bound zeolite catalyst used in the process of the present invention comprises first crystals of a first intermediate pore size zeolite and a binder comprising second crystals of a second zeolite. The use of the second crystals of a second zeolite as a binder results in a catalyst which provides a means for controlling undesirable reactions taking place on or near the external surface of the first zeolite crystals and can have improved mass transfer of hydrocarbon molecules to and from the pores of the first zeolite. In addition, the second zeolite binding crystals, if desired, can also have catalytic activity, can function as a catalyst carrier, and/or can selectively prevent undesirable molecules from entering or exiting the pores of the first zeolite.

Unlike typical zeolite catalysts used in hydrocarbon conversion processes which are normally bound with silica or alumina or other commonly used amorphous binders to enhance the mechanical strength of the zeolite, the zeolite catalyst of the present invention does not contain significant amounts of non-zeolitic binders. Preferably, the zeolite bound zeolite catalyst contains less than 10 percent by weight, based on the weight of the first and second zeolite, of non-zeolitic binders, more preferably contains less than 5 percent by weight, and, most preferably, the catalyst is substantially free of non-zeolitic binder. Preferably, the second zeolite crystals bind the first zeolite crystals by adhering to the surface of the first zeolite crystals thereby forming a matrix or bridge structure which also holds the first crystals particles together. More preferably, the second zeolite particles bind the first zeolite by intergrowing so as to form a coating or partial coating on the larger first zeolite crystals and, most preferably, the second zeolite crystals bind the first zeolite crystals by intergrowing to form an attrition resistant over-growth over the first zeolite crystals.

Although the invention is not intended to be limited to any theory of operation, it is believed that one of the advantages of the zeolite bound zeolite catalyst of the present invention is obtained by the second zeolite crystals controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity and structure type of the second zeolite can be carefully selected, the second zeolite does not significantly adversely affect the reactants exiting the pores of the first zeolite which can occur with conventionally bound zeolite catalysts and may beneficially affect the reactants exiting the pores of the first zeolite. Still further, since the second zeolite is not amorphous but, instead, is a molecular sieve, hydrocarbons may have increased access to the pores of the first zeolite during hydrocarbon conversion processes. Regardless of the theories proposed, the zeolite bound zeolite catalyst, when used in catalytic processes, has the improved properties which are disclosed herein.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia absorption.

The first zeolite used in the zeolite bound zeolite catalyst is an intermediate pore size zeolite. Intermediate pore size zeolites have a pore size from about 5 to about 7 Å and include, for example, MI, MEL, MFS, MEI, MTW, EUO, MTT, HEU, FER, and TON structure type zeolites. These zeolites are described in "Atlas of Zeolite Structure Types", eds. W. H. Meier and D. H. Olson, Butterworth-Heineman, Third Edition, 1992, which is hereby incorporated by reference. Examples of specific intermediate pore size zeolites include ZSM-5, ZSM-11, ZSM-12, ZSM-22, ZSM-23, ZSM-34, ZSM-35, ZSM-38, ZSM-48, ZSM-50, and ZSM-57.

The term "average particle size" as used herein, means the arithmetic average of the diameter distribution of the crystals on a volume basis.

The average crystal size of the crystals of the first zeolite is preferably from about 0.1 micron to about 15 microns, more preferably from about 1 to about 6 microns.

Procedures to determine crystal size are know to persons skilled in the art. For instance, crystal size may be determined directly by taking a suitable scanning electron microscope (SEM) picture of a representative sample of the crystals.

Intermediate pore size zeolites suitable for use in the zeolite bound zeolite catalyst preferably comprise a composition having the following molar relationship:

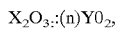

$$X_2O_3:(n)YO_2,$$

wherein X is a trivalent element, such as aluminum, boron and/or gallium, Y is a tetravalent element such as silicon, tin, and/or germanium; and n has a value greater than 10, said value being dependent upon the particular type of zeolite and the trivalent element present in the zeolite. When the intermediate pore size zeolite is a MFI structure type zeolite, n is preferably greater than 20.

As known to persons skilled in the art, the acidity of a zeolite can be reduced using many techniques such as by steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the first zeolite is an aluminosilicate zeolite, the first zeolite will preferably have a silica to alumina mole ratio from 70:1 to 1000:1.

When the first zeolite is a gallium silicate zeolite, the zeolite preferably comprises a composition having the following molar relationship:

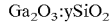

$$Ga_2O_3:ySiO_2$$

wherein y is between about 24 and about 500. The zeolite framework may contain only gallium and silicon atoms or may also contain a combination of gallium, aluminum, and silicon. When the first zeolite is a MFI structure type gallium silicate zeolite, the second zeolite will preferably be an intermediate pore size zeolite having a silica to gallia mole ratio greater than 100. The second zeolite can also have higher silica to gallia mole ratios, e.g., greater than 200, 500, 1000, etc.

The second zeolite will preferably be an intermediate pore size zeolite and have less acid activity than the first zeolite. For instance, when the second zeolite is an intermediate pore size aluminosilicate zeolite, the second zeolite will preferably have a silica to alumina mole ratio greater than 200:1. The second zeolite can also have higher silica to alumina mole ratios, e.g., 500:1, 1,000:1 etc. The second zeolite can also be silicalite, i.e., a MFI type substantially free of alumina or silicalite 2, i.e., a MEL type substantially free of alumina. Preferably the second zeolite will have the same structure type as the first zeolite. The second zeolite is usually present in the zeolite bound zeolite catalyst system in an amount in the range of from about 10% to 60% by weight based on the weight of the first zeolite and, more preferably from about 20% to about 50% by weight.

The second zeolite crystals preferably have a smaller size than the first zeolite crystals. The second zeolite crystals preferably have an average particle size of less than 1 micron, more preferably from about 0.1 to about 0.5 micron. The second zeolite crystals bind the first zeolite crystals. The second zeolite crystals preferably intergrow and form an over-growth which coats or partially coats the first zeolite crystals. Preferably, the coating will be resistant to attrition.

When use to isomerize feeds containing ethylbenzene, the zeolite bound zeolite catalyst will preferably contain at least one hydrogenation metal. Examples of such metals include the oxide, hydroxide, sulfide, or free metal (i.e., zero valent) forms of Group VIII metals (i.e., Pt, Pd, Ir, Rh, Os, Ru, Ni, Co, and Fe), Group IVB metals (i.e., Sn and Pb), Group VB metals (i.e., Sb and Bi), and Group VIIA metals (i.e., Mn, Tc, and Re). Noble metals (i.e., Pt, Pd, Ir, Rh, Os, and Ru) are preferred. Combinations of catalytic forms of noble or non-noble metals, such as combinations of Pt with Ni, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The amount of metal present in the zeolite bound zeolite catalyst will be an effective amount which will generally be from about 0.001 to about 10 percent by weight and, preferably 0.05 to 3.0 percent by weight. The amount will vary with the nature of the metal, less of the highly active metals, particularly platinum, being required than of the less active metals.

The hydrogenation metal may be incorporated into the zeolite bound zeolite catalyst by ion exchange and impregnation. Another way of incorporating the metal into the zeolite bound zeolite catalyst is to include at least a portion of the metal in the synthesis mixture of the second zeolite and then crystallize the metal with the second zeolite. Best results have been achieved by including the metal in the silica binder of a silica bound zeolite extrudate as the binder is being formed and then converting the silica to the second zeolite. The metal may be present on the surface of either or both zeolites and may also be present in the intracrystalline matrix of either or both zeolites.

The zeolite bound zeolite catalyst is preferably prepared by a three step procedure whereby the hydrogenation metal is incorporated into the zeolite bound zeolite during the preparation of the amorphous binder which is subsequently converted to the second zeolite. The first step involves the synthesis of the intermediate pore size first zeolite. Process for preparing the first zeolite are known to persons skilled in the art. For example, with respect to the preparation of an aluminosilicate zeolite or a gallium silicate zeolite having a MFI structure type, one process comprises preparing a solution containing tetrapropyl ammonium hydroxide or bromide, alkali metal oxide, an oxide of aluminum or an oxide of gallium, an oxide of silicon and water, heating the reaction mixture to a temperature of 80° C. to 200° for a period of from about four hours to eight days. The resulting gel forms solid crystal particles which are separated from the reaction medium, washed with water and dried. The resulting product can be calcined in air at temperatures of 400° C.–550° C. for a period of 10–40 hours to remove tetrapropylammonium (TPA) cations.

In the second step, a silica-bound zeolite is prepared by mixing a mixture comprising the first zeolite crystals, a silica gel or sol, water, and optionally the hydrogenation metal, and optionally an extrusion aid, until a homogeneous composition in the form of an extrudable paste develops. The silica binder used in preparing the silica bound zeolite aggregate is preferably a silica sol and can contain various amounts of trivalent elements, e.g., aluminum or gallium. The amount of silica used is such that the content of the zeolite in the dried extrudate at this stage will range from about 40 to 90% by weight, more preferably from about 50 to 80% by weight, with the balance being primarily silica, e.g. about 20 to 50% by weight silica.

The resulting paste is then molded, e.g., extruded, and cut into small strands, e.g., approximately 2 mm diameter extudates, which are dried at 100° C. to 150° C. for a period of 4–12 hours and then are calcined in air at a temperature of from about 400° C. to 550° C. for a period of from about 1 to 10 hours.

Optionally, the silica-bound aggregate can be made into very small particles which have application in fluid bed processes such as catalytic cracking. This preferably involves mixing the zeolite with a silica and metal containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. N.Y., 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound zeolite to a second zeolite which binds the first zeolite crystals together.

To prepare the second zeolite, the silica-bound aggregate is first aged in an appropriate aqueous solution at elevated temperature. Next, the contents of the solution and the temperature at which the aggregate is aged are selected to convert the amorphous silica binder into the desired second zeolite. The newly-formed second zeolite is produced as crystals. The crystals may grow on and/or adhere to the first zeolite crystals, and may also be produced in the form of new intergrown crystals, which are generally much smaller than the first crystals, e.g., of sub-micron size. These newly formed crystals may grow together and interconnect.

The nature of the zeolite formed in the second synthesis conversion of the silica to zeolite may vary as a function of the composition of the secondary synthesis solution and synthesis aging conditions. The secondary synthesis solution is preferably an aqueous ionic solution containing a source of hydroxy ions sufficient to convert the silica to the desired zeolite. It is important, however, that the aging solution be of a composition which will not cause the silica present in the bound zeolite extrudate to dissolve out of the extrudate.

The first zeolite of the catalyst used in the process of the present invention is preferably at least partially in the hydrogen form. Preferably, hydrogen ions are incorporated into the zeolite by exchange of the alkali metal with intermediate ammonium, followed by calcination of the ammonium form to provide the acidic hydrogen form.

The zeolite bound zeolite catalyst used in the process of the present invention can be further treated prior to use. For example, metal/acid activity of the catalyst can be modified by sulfiding. The sulfiding modification can be carried out by presulfiding the catalyst or by adding a sulfur-containing compound to the hydrocarbon feed.

The aromatic hydrocarbon feed mixture employed in the process of the present invention will comprise isomerizable monocyclic alkylaromatic hydrocarbons that preferably contain from two to three alkyl group substituents on the ring, isomelizable bicyclic alkylaromatic hydrocarbons that preferably contain from two to four alkyl group substituents on the rings. These hydrocarbons include:

(A) monocyclic alkylaromatic hydrocarbons represented by the formula:

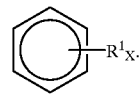

I wherein:
$R^1$ is a alkyl group having 1 to about 4 carbon atoms; and,
X is integer of from 2 to 3 and equals the number of alkyl groups;

(B) bicyclic alkylaromatic hydrocarbons represented by the formula:

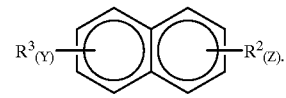

II wherein
$R^2$ and $R^3$ are independently selected from an alkyl group having 1 to about 4 carbon atoms:
Y is an integer of from 0 to 2;
Z is an integer of from 0 to 2;
wherein the sum of Y and Z is an integer in the range of from 1 to 4 and equals total the number of alkyl groups.

$R^1$, $R^2$, and $R^3$ can be straight or branch chained alkyl groups. Examples of suitable alkyl groups include methyl, ethyl, n-propyl, n-butyl, isopropyl, isobutyl, or any combination thereof. The preferred group is methyl.

Suitable monocyclic alkylaromatic hydrocarbons include, for example, xylenes such as para-xylene, ortho-xylene, and meta-xylene, diethylbenzenes such as 1,4-diethylbenzene, 1,2-diethylbenzene, and 1,3-diethylbenzene, trimethylbenzenes such as mesitylene (1,3,5-trimethylbenzene), hemimellitene (1,2,3-trimethylbenzene), and pseudocumene (1,2, 4-trimethylbenzene), ethyltoluenes, triethylbenzenes such as 1,3,5-triethylbenzene, methylpropylbenzenes, ethylpropylbenzenes, dipropylbenzenes, diisopropylbenzenes, triisopropylbenzenes, etc., and mixtures thereof. Suitable bicyclic alkylaromatic hydrocarbons include 1-ethylnaphthalene, 2-methylnaphthalene, dialkylnaphthalenes such as 1,2-dimethylnaphthalene, 1,2-diethylnaphthalene 2,3-dimethylnaphthalene, 2,3-dipropylnaphthalene 2,6-dimethylnaphthalene, 2,6-dibutylnaphthalene, and the like.

The alkylaromatic hydrocarbon feed mixture may consist only of alkylaromatic hydrocarbons or may be a mixture of the alkylaromatic hydrocarbons with other aromatic hydrocarbons such as ethylbenzene and toluene.

The present invention finds particular application with aromatic $C_8$ mixtures containing ethylbenzene and xylenes. Such mixtures will usually have an ethylbenzene content in the range of 5 to 50 weight %, and ortho-xylene content in the range of 0 to 35 weight %, a meta-xylene content in the approximate range of 20 to 95 weight %, and a para-xylene content in the range of 0 to 15 weight %. The feed may also contain non-aromatic hydrocarbons, such as paraffins and naphthenes. The paraffins will generally comprise 0 to 10 weight percent of the feed and usually the paraffins will comprise $C_8$–$C_9$ paraffins.

In carrying out the process of the invention, the aromatic feeds are contacted with the zeolite bound zeolite catalyst under conversion conditions. These conversion conditions include a temperature in the range from about 400°–1000° F., preferably from 750°–925° F., and a pressure in the range of from about 0 to about 1000 (psig), preferably 50–500 (psig), a hydrogen/hydrocarbon molar ratio between about 0.1 to about 10, preferably 0.25 to 5, and a WHSV of between about 0.2 to about 100 and preferably between about 1 to about 10.

Usually the xylene isomerization reaction is carried out in a fixed bed reactor containing the zeolite bound zeolite catalyst. In another embodiment, the xylene isomerization process is carried out in sequential beds using two catalysts. In this embodiment, each catalyst can be in a separate bed or one of the catalysts can form one part of a bed while the second catalyst will form the remaining part of the bed. In this embodiment, the zeolite bound zeolite catalyst will preferably comprise first crystals of an acidic first zeolite bound by second crystals of a second zeolite which has less acidity than the first zeolite and, more preferably, the second zeolite will be substantially nonacidic. The zeolite bound zeolite catalyst will be used primarily to convert ethylbenzene and preferably will be upstream with respect to the second catalyst. The second catalyst will be used to primarily isomerize xylene components in the $C_8$ aromatic feed. The second catalyst can be any catalyst which is suitable for use in xylene isomerization. Examples of catalysts suitable for xylene isomerization include zeolite bound zeolite catalysts, zeolite catalysts bound by amorphous material (silica, alumina, etc.), and acidic non-zeolitic catalysts. In this embodiment, the zeolite bound zeolite catalyst used to convert ethylbenzenes present in the feed will preferably comprise from about 10 percent to about 90 percent of the bed volume.

When a zeolite bound zeolite catalyst is used as the second catalyst, in a preferred embodiment, the first zeolite of the catalyst will have less acidity than the second zeolite and the average particle size of the first crystals will be less than the average particle size of the first crystals of the zeolite bound zeolite first catalyst. In this embodiment, the average particle size of the first crystals of the second catalyst will be from about 0.5 to about 6.0 microns and more preferably from about 0.5 to about 2.0 microns.

By carrying out the process of the present invention, a resulting product is produced which contains p-xylene in an amount at least approaching thermodynamic equilibrium while ethylbenzene present in the feedstream is substantially converted, i.e., at least 30% conversion of ethylbenzene is converted. These conversions are carried out with low aromatics ring loss.

The following examples illustrate the invention:

EXAMPLE 1

Preparation of zeolite bound MFI type gallium silicate catalyst.

I. Catalyst A—Platinum loaded during synthesis.

MFI structure gallium silicate crystals were prepared as follows:

| Components Use for Preparation | Quantity (Grams) |
|---|---|
| Solution A | |
| NaOH pellets (98.6%) | 18.82 |
| $Ga_2O_3$ (99.999%) | 12.06 |
| Water | 50.08 |
| Rinse Water | 189.80 |
| Solution B | |
| Colloidal Silica (Ludox HS-40) | 773.06 |
| Solution C | |
| Tetrapropylammonium bromide | 123.73 |
| Water | 425.01 |
| Rinse Water | 124.97 |
| Solution D | |
| Aqueous Suspension of Colloidal Silicalite with 0.0794 wt. % Seeds | 2.39 |
| Rinse Water | 100.00 |

The ingredients of Solution A were dissolved by boiling until a clear solution was obtained. Solution A was then cooled to ambient temperature and water loss from boiling was corrected.

Solution B was poured into a 2 liter glass beaker. Solution C was poured into the contents of the beaker and mixed. Solution D was then poured into the contents of the beaker and the beaker content was mixed. The contents of the beaker were poured into a 2 liter stainless steel autoclave. Rinse Water was used to rinse the beaker and added to the autoclave. Solution A were added to the autoclave. The contents of the autoclave were mixed about 20 minutes. A smooth pourable gel was obtained. The gel had the following composition expressed in moles of pure oxide:

0.45 $Na_2O$/0.90 TPA Br/0.125 $Ga_2O_3$/10$SiO_2$/147 $H_2O$ the gel contained 1.0 wt ppm of colloidal silicalite seeds.

The autoclave was placed in an oven and heated to 150° C. in 2 hours and maintained at 150° C. at this temperature for 48 hours.

The product was removed from the autoclave and divided into 3 portions. Each portion was washed 7 times with about 600 grams of water. The product was dried over night at 120° C. The amount of product recovered was 333.70 grams. The product was calcined in air at 475° C. for 48 hours. The characteristics of the calcined product were the following:

XRD: Pure MFI
SEM: 4 micron size spherical crystals
Elemental: $SiO_2$/$Ga_2O_3$=80

A portion of the calcined product was formed into silica bound 2 mm extrudates as follows:

| Components Used for Preparation | Quantity (Grams) |
|---|---|
| Silica Sol (Nyacol 2034 DI) | 128.59 |
| Silica gel (aerosil 300) | 12.26 |
| $H_2PtCl_6·6H_2O$ | 2.47 |
| Water | 35.01 |
| Rinse Water | 3.00 |
| Gallium silicate MFI Crystals | 130.00 |

-continued

| Components Used for Preparation | Quantity (Grams) |
|---|---|
| Extrusion Aid (hydroxypropyl methyl cellulose) | 0.87 |

The components were mixed in a food mixer in the order shown. After adding the extrusion aid and mixing for about 7 minutes, a thick and smooth paste was obtained. The paste was extruded into 2 mm extrudates and dried at ambient temperature for 3 hours. The extrudates were broken into smaller 5 mm pieces and dried in an oven at 120° C. for 16 hours. The dried extrudates were calcined at 490° C. for 8 hours in air.

Composition of calcined silica bound extrudate:
Silica binder: 30.1 wt. %
MFI: 69.4 wt. %
Platinum 0.5 wt. %

The silica bound extrudates were converted into zeolite bound zeolite as follows:

| Components Used for Preparation | Quantity (Grams) |
|---|---|
| Solution A | |
| NaOH pellets (98.6%) | 1.36 |
| Water | 29.08 |
| Rinse Water | 11.78 |
| Solution B | |
| Tetrapropylammonium bromide | 9.28 |
| Water | 30.35 |
| Rinse Water | 22.16 |

Solutions A and B were poured into a 1 liter autoclave and mixed. Finally, 70.0 grams of the silica bound extrudates were added to the autoclave. The molar composition of the synthesis mixture was:
048Na$_2$O/1.00TPABr/10S$_i$O$_2$/149H$_2$O The autoclave was placed into an oven. The oven was heated from room temperature to 150° C. in 2 hours and maintained at this temperature for 80 hours. The resulting product was washed at 60° C. 4 times with 1700 ml of water. The conductivity of the last wash water was 49 micros Siemans/cm. The extrudates were dried at 120° C. and calcined in air at 490° C. for 16 hours.

The product was analyzed by XRD and SEM with the following results:

| | |
|---|---|
| XRD: | Excellent crystallinity |
| SEM: | 4 micron size crystals coated with smaller size crystals. No visible amorphous silica. |
| Elemental: | Core crystals:SiO$_2$/Ga$_2$O$_3$ = 80 |
| | Binder crystals = silicalite |
| | Core crystals = 70 wt. % |
| | Platinum = .5 wt. % |

Platinum distribution and platinum particle size were determined by qualitatively examining a sample of the product by transmission electron microscopy (TEM). The platinum was distributed well. The major proportion of the platinum had a particle size of 5–10 nm.

II. Catalyst B—Platinum loaded by pore filling

A portion of the calcined MFI structure type gallium silicate used to prepare Catalyst A was formed into silica bound 2 mm extrudates as follows:

| Components Used for Preparation | Quantity (Grams) |
|---|---|
| Gallium-silicate MFI crystals | 130.05 |
| Water | 37.70 |
| SlO$_2$ gel (aerosil 300) | 45.26 |
| Silica Sol (NALCOAG 1034A) | 128.57 |
| Extrusion aid (hydroxypropyl methyl cellulose) | 0.89 |

The above components were mixed in a food mixer in the order shown. After adding the extrusion aid and mixing for about 14 minutes, a thick and smooth paste was obtained. The paste was extruded into 2 mm extrudates. The extrudates were dried at 150° C. for 7 hours and then calcined in air at 510° C. for 8 hours.

Composition of calcined silica-bound extrudates:
MFI: 70.0 wt. %
S$_i$O$_2$ binder: 30.0 wt. %

The silica bound extrudates were converted into zeolite bound zeolite as follows:

| Components Used for Preparation | Quantity (Grams) |
|---|---|
| Solution A | |
| NaOH pellets (98.6%) | 2.44 |
| Water | 51.91 |
| Rinse Water | 21.08 |
| Solution B | |
| Tetrapropylammonium bromide | 16.56 |
| Water | 54.20 |
| Rinse Water | 39.54 |

Solution A and B were poured into a 300 ml stainless steel autoclave and were mixed. Finally, 125.00 grams of the silica-bound MFI extrudates were added to the autoclave. The molar composition of the synthesis mixture was:
0.48Na$_2$O/0.99 TPA Br/SiO$_2$/148H$_2$O In this mixture, the silica is present as the binder is the extrudate.

The autoclave was placed into an oven at room temperature, heated to 150° C. within 2 hours, and maintained at 150° C. for 72 hours. The resulting product was washed at 60° C. with 7 portions of 2000 ml of water. The conductivity of the last wash water was 25 μS/cm. The product was dried at 150° C. and calcined in air at 500° C. for 16 hours.

The resulting product was characterized by x-ray diffraction (XRD) and scanning electron microscopy (SEM) with the following results:

| | |
|---|---|
| XRD: | Excellent crystallinity |
| SEM: | 4 micron MFI crystals coated with smaller size crystals. No visible amorphous silica. |
| Elemental: | Core crystals:SiO$_2$/Ga$_2$O$_3$ = 80 |
| | Binder crystals = silicalite |
| | Core crystals = 70 wt. % |
| | Binder crystals = 30 wt. % |

An amount of 0.31 wt. % of platinum (based on the weight of is product) was loaded into the catalyst. The process was carried out by first exchanging the catalyst at 65° C. with a 1 normal NH$_4$Cl solution. The exchanged catalyst was washed with water, dried, and then calcined at 530° C. for 8 hours. The loading of the platinum was done by the pore-filling method with an appropriate amount of Pt $(NH_3)_4Cl_2$ dissolved in water. After loading, the catalyst was dried and calcined at 480° C. for 8 hours.

Platinum distribution and platinum particle size were determined by qualitatively examining a sample of the product by transmission electron microscopy (TEM). The platinum particle size was predominantly 10–30 nm and platinum was not as well distributed as Catalyst A.

EXAMPLE 2

A series of isomerization reactions were conducted using Catalyst A by passing an artificial feed through a fixed bed reactor. Catalyst A was pretreated in $H_2$ for two (2) hours at 850° F. and 250 psig. After the temperature had been lowered to 700° F., the catalyst was presulfided to breakthrough with about 500 ppm $H_2S$ in $H_2$ at 250 psig. The tests were run at varying conditions. The conditions and results are shown in Table I below:

TABLE I

| | Run No. | | | | |
|---|---|---|---|---|---|
| | 1 | 2 | 3 | 4 | 5 |
| Temperature (° F.) | 750 | 750 | 750 | 795 | 750 |
| HC Partial Pressure (inlet) | 163 | 118 | 118 | 118 | 163 |
| $H_2$ Partial Pressure (inlet) | 81 | 118 | 118 | 118 | 81 |
| WHSV (#/#/Hr) | 10 | 3.7 | 10 | 20 | 10 |
| $H_2$:Oil Ratio (Molar) | 0.5 | 1.0 | 1.0 | 1.0 | 0.5 |
| Hours On-Oil | 155 | 431 | 481 | 621 | 748 |
| Feed EB Wt. % | 11.4 | 12.6 | 12.6 | 12.6 | 12.6 |
| Feed Xylenes Wt. % | 86.8 | 85.3 | 85.3 | 85.3 | 85.3 |
| Feed PX Wt. % | 2.7 | 1.1 | 1.1 | 1.1 | 1.1 |
| % EB reacted | 73.7 | 93.5 | 73.0 | 74.3 | 74.7 |
| Ring Loss (% of feed aromatic rings) | 0.1 | *−0.1 | *−0.1 | *−0.2 | *−0.2 |
| Xylenes Loss (% of feed xylenes) | 2.0 | 5.9 | 2.3 | 2.5 | 2.5 |
| PX approach to equilibrium (%) | 103 | 101 | 101 | 98 | 100 |

*Negative values believed due to minor gas chromatography variations.

The percent, % EB reacted was determined by the formula: % EB Conv=100× [EB in-EB out] divided by EB in; Aromatics ling loss % was determined by the formula: 100× (moles of aromatics in feed—moles of aromatics in product)/(moles of aromatics in feed). Loss of xylenes was determined by the formula: 100× (moles of xylenes in feed—moles of xylenes in product)/(moles of xylenes in feed) and PX approach to equilibrium was determined by the formula: (Product PX/Xs-Feed PX/Xs)/(Equilibrium PX/Xs-FeedPX/Xs) X 100.

EXAMPLE 3

A series of isomerization reactions were conducted using Catalyst B by passing an artificial feed through a fixed bed reactor. Catalyst B was pretreated in $H_2$ and presulfided using the same procedure described in Example 2. The tests were run at varying conditions. The conditions and results are shown in Table II below:

TABLE II

| | Run No. | | | | |
|---|---|---|---|---|---|
| | 1 | 2 | 3 | 4 | 5 |
| Temperature (° F.) | 736 | 750 | 710 | 786 | 736 |
| HC Partial Pressure | 163 | 118 | 118 | 118 | 118 |

TABLE II-continued

| | Run No. | | | | |
|---|---|---|---|---|---|
| | 1 | 2 | 3 | 4 | 5 |
| $H_2$ Partial Pressure | 81 | 118 | 118 | 118 | 118 |
| WHSV (#/#/Hr) | 10 | 10 | 5 | 20 | 10 |
| $H_2$:Oil Ratio (Molar) | 0.5 | 1.0 | 1.0 | 1.0 | 1.0 |
| Hours On-Oil | 160 | 233 | 633 | 656 | 714 |
| Feed EB Wt. % | 12.3 | 12.6 | 12.6 | 12.6 | 12.6 |
| Feed Xylenes Wt. % | 85.3 | 85.3 | 85.3 | 85.3 | 85.3 |
| Feed PX Wt. % | 7.2 | 1.1 | 1.1 | 1.1 | 1.1 |
| % EB reacted | 72 | 78.3 | 75.8 | 74.0 | 69.4 |
| Ring Loss (% of feed aromatic rings) | 0.1 | 1.3 | 1.2 | 0.6 | 1.0 |
| Xylenes Loss (% of feed xylenes) | 3.3 | 4.2 | 3.7 | 3.4 | 2.9 |
| PX approach to equilibrium (%) | 102 | 101 | 101 | 99 | 101 |

The data in the Tables shows that both Catalysts A and B exhibit high EB removal activity and xylene selectivity with low aromatics ring loss and xylene loss. Both catalysts maintained high activity throughout the tests. Catalyst A was able to convert over 85% of the EB and produce a product containing greater than equilibrium amounts of para-xylene with very low aromatics ring loss. High EB activity and PX selectivity, low aromatics ring loss, and activity maintenance are several of the major criteria for selecting a xylene isomerization catalyst for a commercial operation.

What is claimed is:

1. A process for isomerizing a feed containing isomerizable monocyclic alkylaromatic hydrocarbons, bicyclic alkylaromatic hydrocarbons, or mixtures thereof comprising:

contacting said feed under isomerization conversion conditions with a zeolite bound zeolite catalyst which does not contain significant amounts of non-zeolitic binder and comprises:
   (a) first crystals of a first intermediate pore size zeolite;
   (b) a binder comprising second crystals of a second zeolite.

2. The process recited in claim 1, wherein said second crystals are intergrown and form at least a partial coating on said first crystals.

3. The process recited in claim 2, wherein said first crystals of said first zeolite have an average particle size greater than about 0.1 micron and said second crystals of said second zeolite have an average particle size that is less than said first crystals of said first zeolite.

4. The process recited in claim 3, wherein said alkylaromatic hydrocarbons are selected from the group consisting of:

(a) a monocyclic alkylaromatic hydrocarbon represented by the formula:

I

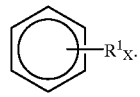

wherein:
   $R^1$ is a alkyl group having 1 to about 4 carbon atoms; and
   X is an integer of from 2 to 3; and
(b) a bicyclic alkylaromatic hydrocarbon represented by the formula:

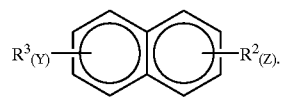

wherein
R² and R³ are independently selected from an alkyl group having 1 to about 4 carbon atoms:
Y is an integer of from zero to 2;
Z is an integer of from zero to 2;
wherein the sum of Y and Z is an integer in the range of from 1 to 4; and,
(c) mixtures thereof.

5. The process recited in claim 4, wherein the structure type of said first zeolite and said second zeolite are independently selected from the group consisting of MFI, MEL, MTW, MTT, FER, EUO, and TON.

6. The process recited in claim 5, wherein said feed comprises monocyclic alkylaromatic hydrocarbons.

7. The process recited in claim 6, wherein R¹ is methyl or ethyl and x is 2.

8. The process recited in claim 5, wherein said alkylaromatic hydrocarbon comprises bicyclic alkylaromatic hydrocarbons.

9. The process recited in claim 8, wherein R² and R³ are methyl, y is 1 and z is 1.

10. The process recited in claim 7, wherein said first zeolite contains catalytically active sites.

11. The process recited in claim 10, wherein said feed is an aromatic $C_8$ mixture of ethylbenzene and xylene in which the paraxylene is less than at thermodynamic equilibrium.

12. The process recited in claim 11, wherein said first zeolite is at least partially in the hydrogen form.

13. The process recited in claim 11, wherein said zeolite bound zeolite catalyst further comprises at least one hydrogenation metal.

14. The process recited in claim 13, wherein said isomerization conditions comprise a temperature in the range of from about 400° to about 1000° F., a pressure in the range of from about 50 to about 1000 psig, a weight hour space velocity of from about 0.5 to about 100, and a $H_2/HC$ molar ratio of between 0.1 to about 10.

15. The process recited in claim 14, wherein said first zeolite and said second zeolite are independently selected from a composition having the following molar relationship:

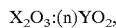

wherein X is aluminum, boron, titanium, and/or gallium, Y is silicon, tin, and/or germanium, and n is at least 10.

16. The process recited in claim 15, wherein said second zeolite has less acidity than said first zeolite.

17. The process recited in claim 16, wherein said second zeolite has a silica to alumina mole ratio greater than about 200:1 or a silica to gallia mole ratio greater than about 100:1.

18. The process recited in claim 17, wherein said first zeolite has a silica to alumina mole ratio of from about 70:1 to about 700:1 or a silica to gallia mole ratio from about 24:1 to about 500:1.

19. The process recited in claim 16, wherein said catalyst is prepared by converting the silica binder of a silica bound aggregate comprising said first crystals of said first zeolite and at least a portion of said at least one hydrogenation metal to said second zeolite.

20. The process recited in claim 16, wherein said zeolite bound zeolite catalyst contains less than 5% by weight of non-zeolitic binder based on weight of said first intermediate pore size zeolite and said second intermediate pore size zeolite.

21. The process recited in claim 15, wherein at least 30% of the ethylbenzene present in said feed is converted.

22. The process recited in claim 21, wherein said first zeolite has an MFI structure.

23. The process recited in claim 22, wherein said second zeolite is has a MFI or MEL structure.

24. The process recited in claim 23, wherein said at least one hydrogenation metal is a Group VIII metal.

25. The process recited in claim 24, wherein the average particle size of the crystals of said first zeolite is from about at least 1 to about 6 microns and the average particle size of the crystals of said second zeolite is from about 0.1 to about 0.5 microns.

26. The process recited in claim 15, wherein said zeolite bound zeolite catalyst is prepared by aging at elevated temperatures a silica-bound aggregate containing said first crystals of said first zeolite in an aqueous ionic solution containing hydroxy ions.

27. The process recited in claim 23, wherein said second zeolite is silicalite or silicalite 2.

28. A process of isomerizing a hydrocarbon feed comprising an aromatic $C_8$ mixture containing ethylbenzene and xylene in which paraxylene is less than thermodynamic equilibrium comprising contacting said feed under conversion conditions with two catalysts wherein the first catalyst is a zeolite bound zeolite catalyst and the second catalyst is suitable for xylene isomerization; wherein said zeolite bound zeolite catalyst does not contain significant amounts of non-zeolitic binder and comprises:
(a) first crystals of an acidic intermediate pore size first zeolite;
(b) a binder comprising second crystals of a second zeolite having less acidity than said first zeolite; and,
(c) an effective amount of a hydrogenation metal.

29. The process recited in claim 28, wherein said second crystals are intergrown and form at least a partial coating on said first crystals.

30. The process recited in claim 29, wherein said first crystals of said first zeolite have an average particle size greater than about 0.1 micron and said second crystals of said second zeolite have an average particle size that is less than said first crystals of said first zeolite.

31. The process recited in claim 30, wherein the structure type of said first zeolite and said second zeolite are independently selected from the group consisting of MFI, MEL, MTW, MTT, FER, EUO, and TON.

32. The process recited in claim 31, wherein said conversion conditions comprise of a temperature in the range of from about 400° to about 1000° F., a pressure in the range of from about 50 to 1000 psig, a weight hour space velocity of from about 0.5 to 100, and a $H_2/HC$ molar ratio of between 0.1 to about 10.

33. The process recited in claim 32, wherein said feed is contacted with said zeolite bound zeolite catalyst before it is contacted with said catalyst suitable for xylene isomerization.

34. The process recited in claim 33, wherein at least 30 percent of the ethylbenzene is converted.

35. The process recited in claim 34, wherein said first zeolite is an aluminosilicate zeolite or a gallium silicate zeolite.

36. The process recited in claim 32, wherein said second zeolite is substantially nonacidic.

37. The process recited in claim 35, wherein at least 50% of the ethylbenzene is converted.

38. The process recited in claim 35, wherein said first catalyst is prepared by converting the silica binder of a silica bound aggregate comprising said first crystals of said first zeolite and at least a portion of said at least one hydrogenation metal to said second zeolite.

39. The process recited in claim 35, wherein said first zeolite has a silica to alumina mole ratio of from about 70:1 to about 700:1 or a silica to gallia mole ratio from about 24:1 to about 500:1.

40. The process recited in claim 39, wherein said second zeolite has a silica to alumina mole ratio greater than about 200:1 or a silica to gallia mole ratio greater than about 200:1.

41. The process recited in claim 35, wherein said zeolite bound zeolite catalyst and said catalyst suitable for xylene isomerization are located in separate catalyst beds.

42. The process recited in claim 35, wherein said zeolite bound zeolite catalyst and said catalyst suitable for xylene isomerization are located in the same reactor.

43. The process recited in claim 35, wherein said zeolite bound zeolite catalyst and said xylene isomerization catalyst are located in the same catalyst bed.

44. The process recited in claim 39, wherein said second catalyst is an acidic non zeolitic catalyst.

45. The process recited in claim 39, wherein said second catalyst is a zeolite catalyst bound by amorphous material.

46. The process recited in claim 40, wherein the average particle size of the crystals of said first zeolite is from about 1 to about 6 microns and the average particle size of said second zeolite is from about 0.1 to about 0.5 micron.

47. The process recited in claim 46, wherein said first zeolite of said zeolite bound zeolite catalyst has an MFI structure.

48. The process recited in claim 47, wherein said second zeolite has a MFI or MEL structure.

49. The process recited in claim 33, wherein said second catalyst is a zeolite bound zeolite catalyst which does not contain significant amounts of non-zeolitic binder and comprises:

(a) first crystals of an intermediate pore size first zeolite; and (b) binder comprising second crystals of a second zeolite having higher acidity than said first zeolite.

50. The process recited in claim 46, wherein said xylene isomerization catalyst comprises a zeolite bound zeolite catalyst which does not contain significant amounts of non-zeolitic binder and comprises:

(a) first crystals of an MFI structure type first zeolite having an average particle size that is less than the average particle size of said first crystals of the zeolite bound zeolite first catalyst; and (b) second crystals of MFI or MEL structure type zeolite having higher acidity than said first zeolite.

51. The process recited in claim 50, wherein said second zeolite bound zeolite catalyst further comprises an effective amount of at least one hydrogenation metal.

52. The process recited in claim 35, wherein said zeolite bound zeolite catalyst is prepared by aging at elevated temperatures a silica-bound aggregate containing said first crystals of said first zeolite in an aqueous ionic solution containing hydroxy ions.

* * * * *